(12) United States Patent
Schmidt (10) Patent No.: US 9,030,283 B2
(45) Date of Patent: May 12, 2015

(54) DOUBLE HELIX CONDUCTOR

(71) Applicant: Lifewave, Inc., San Diego, CA (US)

(72) Inventor: David G. Schmidt, Poway, CA (US)

(73) Assignee: Medical Energetics Ltd, Galway (IE)

( * ) Notice: Subject to any disclaimer, the term of this patent is extended or adjusted under 35 U.S.C. 154(b) by 0 days.

(21) Appl. No.: 14/103,740

(22) Filed: Dec. 11, 2013

(65) Prior Publication Data

US 2014/0097925 A1    Apr. 10, 2014

Related U.S. Application Data (63) Continuation of application No. 13/213,604, filed on Aug. 19, 2011, now Pat. No. 8,653,925.

(60) Provisional application No. 61/464,449, filed on Mar. 3, 2011.

(51) Int. Cl.
| | |
|---|---|
| H01F 27/28 | (2006.01) |
| H01H 1/00 | (2006.01) |
| B21F 3/04 | (2006.01) |
| H01F 41/06 | (2006.01) |
| H01F 5/00 | (2006.01) |
| H05H 7/04 | (2006.01) |
| A61N 2/02 | (2006.01) |
| G21K 1/093 | (2006.01) |

(52) U.S. Cl.
CPC . *H01F 27/28* (2013.01); *A61N 2/02* (2013.01); *G21K 1/093* (2013.01); *H01F 5/00* (2013.01); *H05H 7/04* (2013.01)

(58) Field of Classification Search
USPC ............ 336/188, 189; 242/430, 440.1, 444.2, 242/444.4; 335/213, 214
See application file for complete search history.

(56) References Cited

U.S. PATENT DOCUMENTS

| | | | |
|---|---|---|---|
| 2,035,274 A | 3/1936 | Mougey | 173/265 |
| 3,066,295 A | 11/1962 | Krause et al. | 343/874 |
| 3,760,812 A | 9/1973 | Timm et al. | 128/418 |
| 3,774,452 A | 11/1973 | Tullos et al. | 73/418 |
| 4,266,532 A | 5/1981 | Ryaby et al. | 128/1.5 |
| 4,439,702 A | 3/1984 | Belikov et al. | 310/80 |
| 4,489,276 A | 12/1984 | Yu | 324/338 |
| 4,832,051 A | 5/1989 | Jarvik et al. | 128/784 |
| 5,077,934 A | 1/1992 | Liboff et al. | 47/1.3 |
| 5,079,458 A | 1/1992 | Schuster | 310/12 |
| 5,173,669 A | 12/1992 | Manoly | 333/162 |
| 5,359,340 A | 10/1994 | Yokota | 343/792 |
| 5,366,493 A | 11/1994 | Scheiner et al. | 607/116 |
| 5,464,456 A | 11/1995 | Kertz | 47/1.3 |
| 5,654,723 A | 8/1997 | Craven et al. | 343/742 |
| 5,819,467 A | 10/1998 | Zucker | 47/1.3 |
| 5,892,480 A | 4/1999 | Killen | 343/385 |
| 5,909,165 A | 6/1999 | Leupold | 335/210 |

(Continued)

FOREIGN PATENT DOCUMENTS

| | | |
|---|---|---|
| GB | 479841 | 2/1938 |
| GB | 2480610 | 11/2011 |

(Continued)

*Primary Examiner* — Tsz Chan
(74) *Attorney, Agent, or Firm* — Pillsbury Winthrop Shaw Pittman LLP (57) ABSTRACT

An electrical system having an underlying structure resembling the double helix most commonly associated with DNA may be used to produce useful electromagnetic fields for various application.

16 Claims, 9 Drawing Sheets

(56) References Cited

U.S. PATENT DOCUMENTS

| | | | |
|---|---|---|---|
| 5,954,630 A | 9/1999 | Masaki et al. | 600/28 |
| 6,005,462 A | 12/1999 | Myers | 335/220 |
| 6,169,523 B1 | 1/2001 | Ploussios | 343/895 |
| 6,239,760 B1 * | 5/2001 | Van Voorhies | 343/742 |
| 6,300,920 B1 | 10/2001 | Pertl et al. | 343/895 |
| 6,552,530 B1 * | 4/2003 | Vaiser et al. | 324/204 |
| 6,770,023 B2 | 8/2004 | Vaiser et al. | 600/13 |
| 6,921,042 B1 | 7/2005 | Goodzeit et al. | 242/430 |
| 7,148,783 B2 | 12/2006 | Parsche et al. | 336/225 |
| 7,154,368 B2 | 12/2006 | Sweeney et al. | 336/229 |
| 7,375,449 B2 | 5/2008 | Butterfield | 310/207 |
| 8,463,407 B2 | 6/2013 | Bulkes et al. | 607/148 |
| 8,652,023 B2 | 2/2014 | Schmidt | 600/13 |
| 8,653,925 B2 | 2/2014 | Schmidt | 336/188 |
| 8,749,333 B2 | 6/2014 | Schmidt | 336/73 |
| 8,919,035 B2 | 12/2014 | Schmidt | |
| 2005/0121396 A1 | 6/2005 | Kosakewich | 210/748 |
| 2008/0161884 A1 | 7/2008 | Chandler et al. | 607/50 |
| 2008/0266203 A1 | 10/2008 | Rossetto et al. | 345/895 |
| 2009/0206974 A1 | 8/2009 | Meinke | 336/224 |
| 2010/0005711 A1 | 1/2010 | McNeff | 47/1.4 |
| 2010/0057655 A1 | 3/2010 | Jacobson et al. | 706/45 |
| 2010/0179630 A1 | 7/2010 | Williams | 607/127 |
| 2012/0223800 A1 | 9/2012 | Schmidt | 336/229 |
| 2013/0192129 A1 | 8/2013 | Schmidt | 471/1.3 |
| 2013/0211181 A1 | 8/2013 | Schmidt | 600/13 |
| 2013/0285782 A1 | 10/2013 | Schmidt | 336/73 |
| 2014/0097925 A1 | 4/2014 | Schmidt | |
| 2014/0100412 A1 | 4/2014 | Schmidt | 600/13 |
| 2014/0218149 A1 | 8/2014 | Schmidt | 336/73 |
| 2014/0371514 A1 | 12/2014 | Schmidt | |

FOREIGN PATENT DOCUMENTS

| | | |
|---|---|---|
| WO | WO 2012/118971 | 9/2012 |
| WO | WO 2013/112810 | 8/2013 |
| WO | WO 2013/123009 | 8/2013 |

* cited by examiner

DOUBLE HELIX CONDUCTOR

RELATED APPLICATIONS

This present application is a continuation of, and claims priority to, U.S. patent application Ser. No. 13/213,604, entitled "Double Helix Conductor," filed Aug. 19, 2011, which claims priority to U.S. Provisional Patent Application Ser. No. 61/464,449, entitled "Novel Electromagnetic Coil With Structure Similar To DNA," filed Mar. 3, 2011. These related applications are hereby incorporated by reference into the present application in their entirety.

FIELD OF THE INVENTION

The invention relates to bodies structured as helically wound runners around which one or more conductive wires may be wound, electrical devices and/or systems configured to include such bodies, and the manufacture of such bodies and/or such electrical devices and/or systems. The invention also relates to methods of operation of these devices and systems, and applications thereof.

BACKGROUND OF THE INVENTION

It is known that spirally wound electrical conductors may exhibit certain electromagnetic properties and/or generate particular electromagnetic fields. For example, it is known that an electromagnetic coil may act as an inductor and/or part of a transformer, and has many established useful applications in electrical circuits. An electromagnetic coil may be used to exploit the electromagnetic field that is created when, e.g., an active current source is operatively coupled to both ends of the coil.

SUMMARY

One aspect of the invention relates to an electrical system comprising a body and one or more conductive wires. The body may include two intertwined helically wound runners. A first runner is coupled to the second runner by struts. The body is arranged in a toroidal shape. The one or more conductive wires may be spirally wound around at least one runner of the body.

These and other objects, features, and characteristics of the present disclosure, as well as the methods of operation and functions of the related components of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the any limits. As used in the specification and in the claims, the singular form of "a", "an", and "the" include plural referents unless the context clearly dictates otherwise.

DETAILED DESCRIPTION

Figure 1:
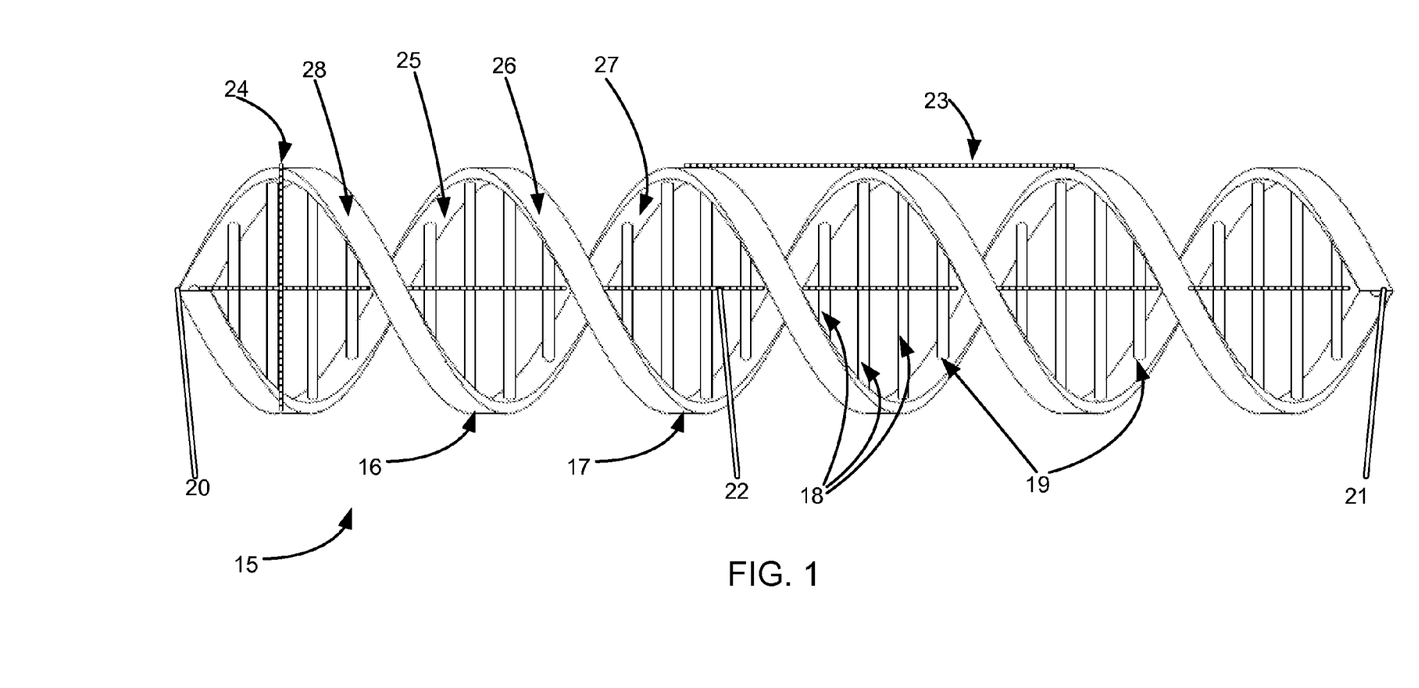
FIG. 1 illustrates a side view of an exemplary body including two intertwined helically wound runners, coupled by struts.

FIG. 1 illustrates a side view of an exemplary body 15. Body 15 may include two or more intertwined helically wound runners—runner 16 and runner 17. Runner 16 and runner 17 may be coupled by struts 18. Body 15 include two ends—end 20 and end 21—disposed at opposite sides of body 15. Runners 16 and/or 17 may be arranged in the shape of a three-dimensional curve similar to or substantially the same as a helix. A helix may be characterized by the fact that a tangent line at any point along the curve has a constant angle with a (fixed) line called the axis. The pitch of a helix may be the width of one 360 degree helix turn (a.k.a. revolution), e.g. measured parallel to the axis of the helix. Intertwined helically wound runners may share the same axis, be congruent, and/or differ by a translation along the axis, e.g. measuring half the pitch. The two runners shown in FIG. 1 may share the same axis 22, extending horizontally for approximately three complete revolutions. The length of body 15, as measured along axis 22 from end 20 to end 21, may thus be approximately three times the length of pitch 23. A helical shape may have constant pitch, constant radius (measured in the plane perpendicular to the axis), constant torsion, constant curvature, constant ratio of curvature to torsion, and/or a straight axis. In FIG. 1, the radius of body 15 may be half of diameter 24. It is noted that the shape of body 15 resembles the general shape of DNA.

The shape of the cross-section of a runner may include one or more of a circle, an oval, a square, a triangle, a rectangle, an angular shape, a polygon, and/or other shapes. The width and height of the cross-section of a runner may be limited to a maximum of half the pitch for practical purposes. The shape and/or size of the cross-section of a runner may change along the length of the runner. The relation of the width of a runner to the pitch of the helical shape may define a characteristic measurement/feature of body 15. This relation may be constant along the length of body 15, e.g. from end 20 to end 21. In FIG. 1, the shape of cross-section of runner 16 and runner 17 may be a rectangle that is approximately three times wider than it is tall. Furthermore, the width of runner 16 or runner 17 may be approximately $1/13^{th}$ of the pitch of said runner of body 15. As a result, runner 17 of body 15 resembles a ribbon having an inner surface 25 (facing axis 22 of the helical shape) and an outer surface 26 (facing the opposite way as inner surface 25). Runner 16 of body 15 resembles a ribbon having an inner surface 27 (facing axis 22 of the helical shape) and an outer surface 28 (facing the opposite way as inner surface 27). Note that embodiments of this disclosure are not intended to be limited by any of the given examples.

Struts 18 coupling the runner 16 and runner 17 may be substantially straight, curved, the shape of an arc, twisted, and/or other shapes. In FIG. 1, struts 18 may be substantially straight. Struts 18 may be arranged substantially perpendicular to axis 22, and/or substantially parallel to others of struts 18. The shape of a cross-section of a strut may include one or more of a circle, an oval, a square, a triangle, a rectangle, an angular shape, a polygon, and/or other shapes. The shape and/or size of the cross-section of one of struts 18 may change along the length of the strut. In FIG. 1, the shape of the cross-section of struts 18 may be a circle. In FIG. 1, all or most struts may have substantially the same length. The number of struts per revolution may not be constant. In FIG. 1, body 15 includes approximately 10 struts per complete revolution of 3 runner. As shown in FIG. 1, the diameter of each strut may be smaller than the width of a runner as measured e.g. at inner surface 25 of runner 17 at the point of engagement 19 with one of struts 18. The diameter of one strut may not be constant. The diameters of multiple adjacent struts may not be the same.

Runner 16, runner 17 and/or struts 18 may be manufactured from one or more of plastic, plastic plated with metals including copper, nickel, iron, soft iron, nickel alloys, and/or other metals and alloys, and/or other materials. In some embodiments, runner 16, runner 17 and struts 18 are manufactured from non-conductive material. Runner 16, runner 17, and struts 18 may be manufactured from different materials. Runner 16, runner 17, and struts 18 may be manufactured through integral construction or formed separately prior to being assembled.

Figure 2:
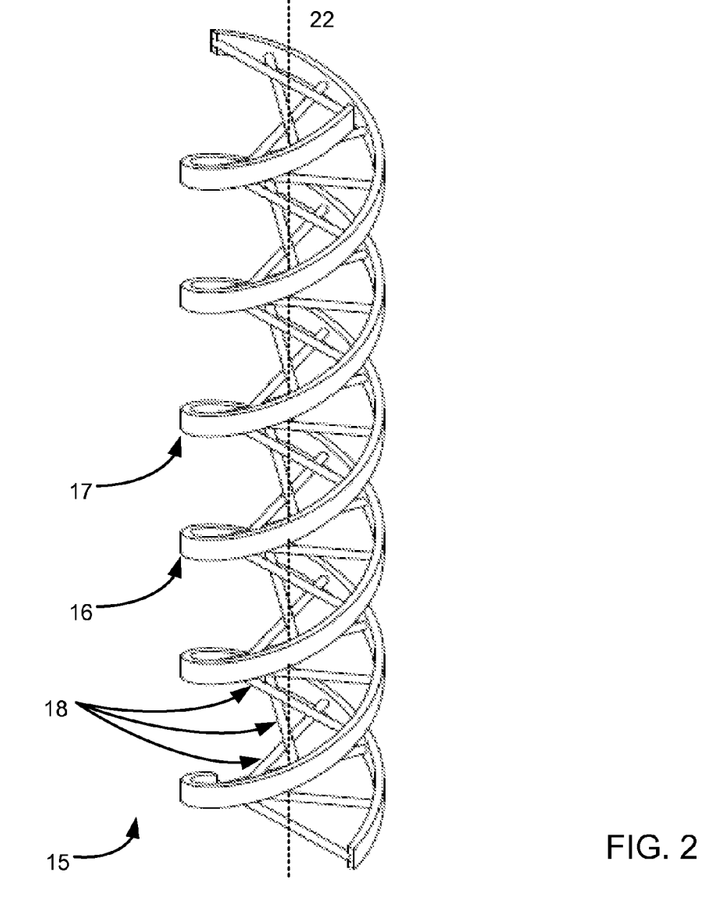
FIG. 2 illustrates an isometric view of an exemplary body including two intertwined helically wound runners, coupled by struts.

FIG. 2 illustrates an isometric view of an exemplary body 15 including two intertwined helically wound runners—runner 16 and runner 17—coupled by struts 18. Body 15 is shown here with axis 22 of both helically wound runners extending vertically.

Figure 3:
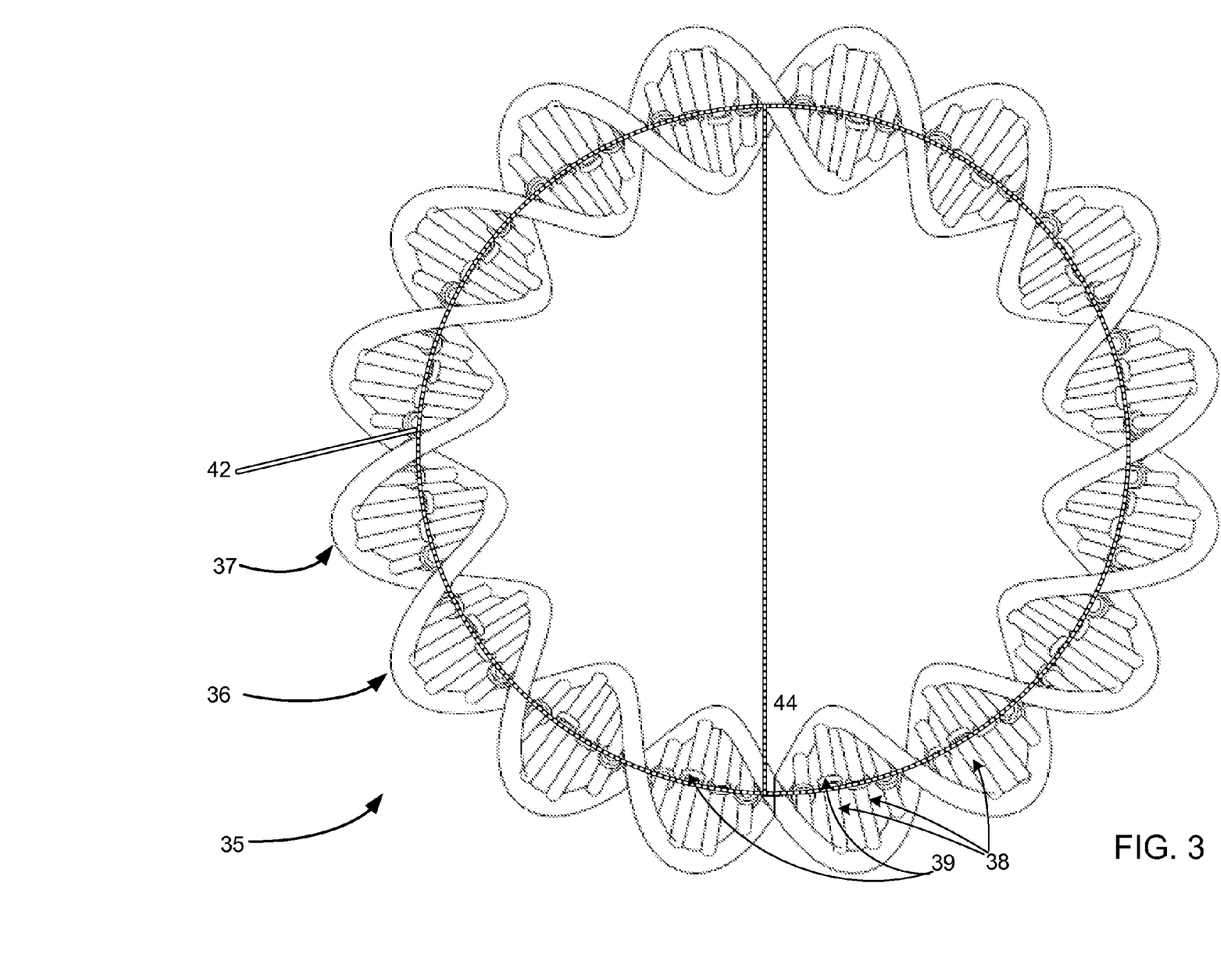
FIG. 3 illustrates a top-down view of an exemplary body including two intertwined helically wound runners sharing the same circular axis, both runners coupled by struts.

FIG. 3 illustrates a top-down view of an exemplary body 35 including two intertwined helically wound runners—runner 36 and runner 37—sharing the same circular axis 42, both runners coupled by struts 38. The resulting shape of body 35 may be referred to as toroidal. Body 35 may be formed the same as or similar to body 15, though comprising more revolutions, by arranging the body in a planar circular shape and joining both ends—end 20 and end 21 in FIG. 1—together. The preceding statement is not intended to limit the (process of) manufacture of bodies similar to or substantially the same as body 35 in any way. Note that the shape of the cross-section of both runner 36 and runner 37 in FIG. 3 may be circular, whereas it may be rectangular for body 15 in FIGS. 1 and 2.

Referring to FIG. 3, the diameter 44 of the circular axis of body 35, as well as the number of complete revolutions per runner required to completely extend along the entire circular axis 42 may be characteristic measurements/features of body 35. For example, as shown in FIG. 3, runner 36 and runner 37 of body 35 may require approximately eight complete revolutions around circular axis 42 of body 35, or some other number of rotations.

Note that one or more struts 38 of body 35 in FIG. 3 include a center-strut element 39, which is lacking from struts 18 of body 15. Center-strut element 39 may be associated with a particular strut of body 35. The shape of the cross section of a center-strut element may include one or more of a circle, an oval, a square, a triangle, a rectangle, an angular shape, a polygon, and/or other shapes. The shape and/or size of the cross-section of one of center-strut elements 39 may change along the length of center-strut element 39. One or more struts 38 of body 35 may include a center-strut element 39, which may have a different shape than a center-strut element 39 of another one of struts 38. In FIG. 3, the shape of the cross-section of center-strut element 39—nay be circular, such that center-strut element 39 may have a cylindrical shape, in which the axis of the cylindrical shape of a given center-strut element 39 may coincide with the associated strut 38. In FIG. 3, struts 38 include center-strut element 39, having substantially the same shape. A center-strut element may enhance structural integrity and/or serve other purposes.

Figure 4:
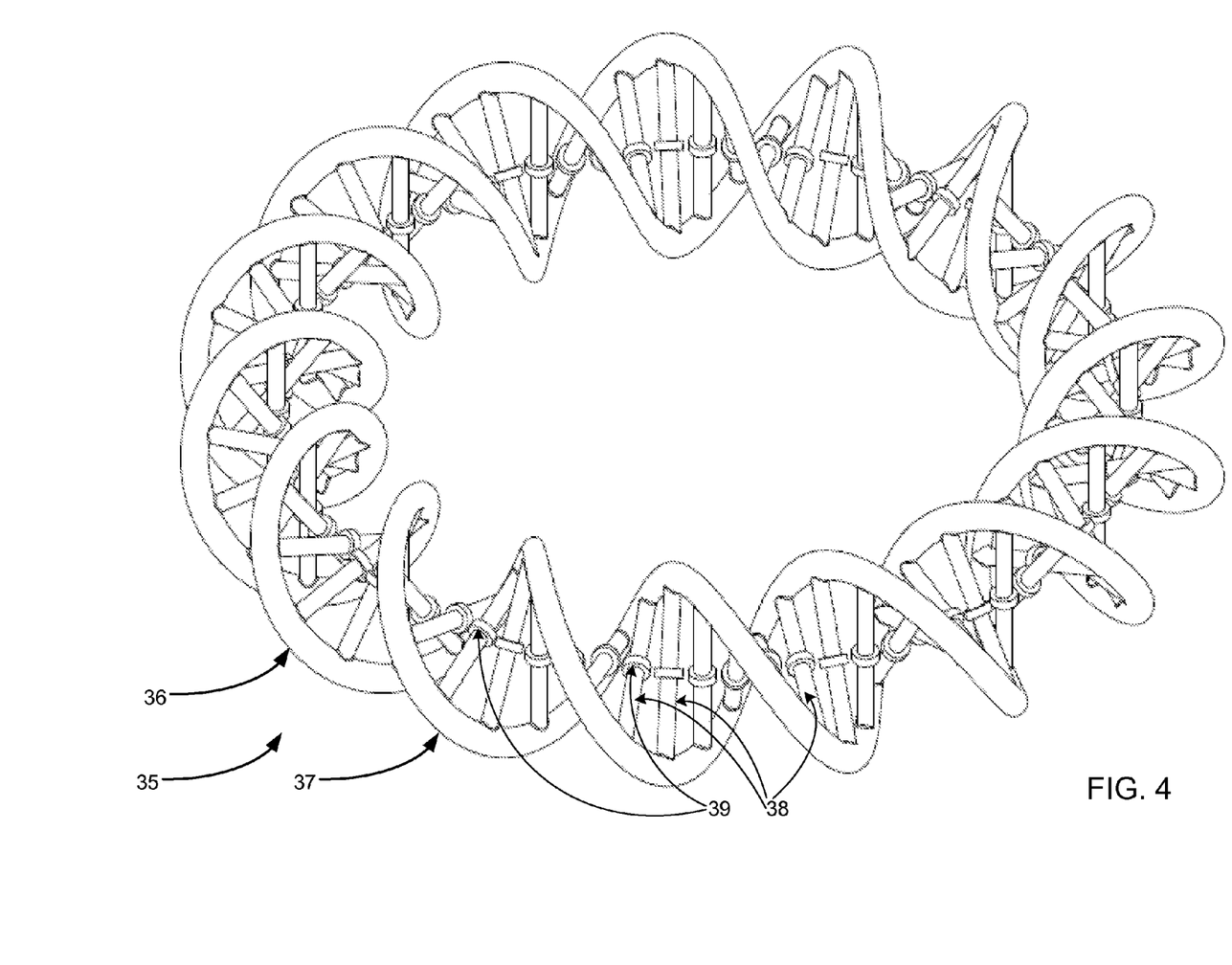
FIG. 4 illustrates an isometric view of an exemplary body including two intertwined helically wound runners sharing the same circular axis, both runners coupled by struts.

FIG. 4 illustrates an isometric view of an exemplary body 35 including two intertwined helically wound runners—runner 36 and runner 37—sharing the same circular axis, both runners coupled by struts 38. Note that, as in FIG. 3, the struts of body 35 in FIG. 4 may include a center-strut element 39, which may be lacking from struts 18 of body 15.

Figure 5:
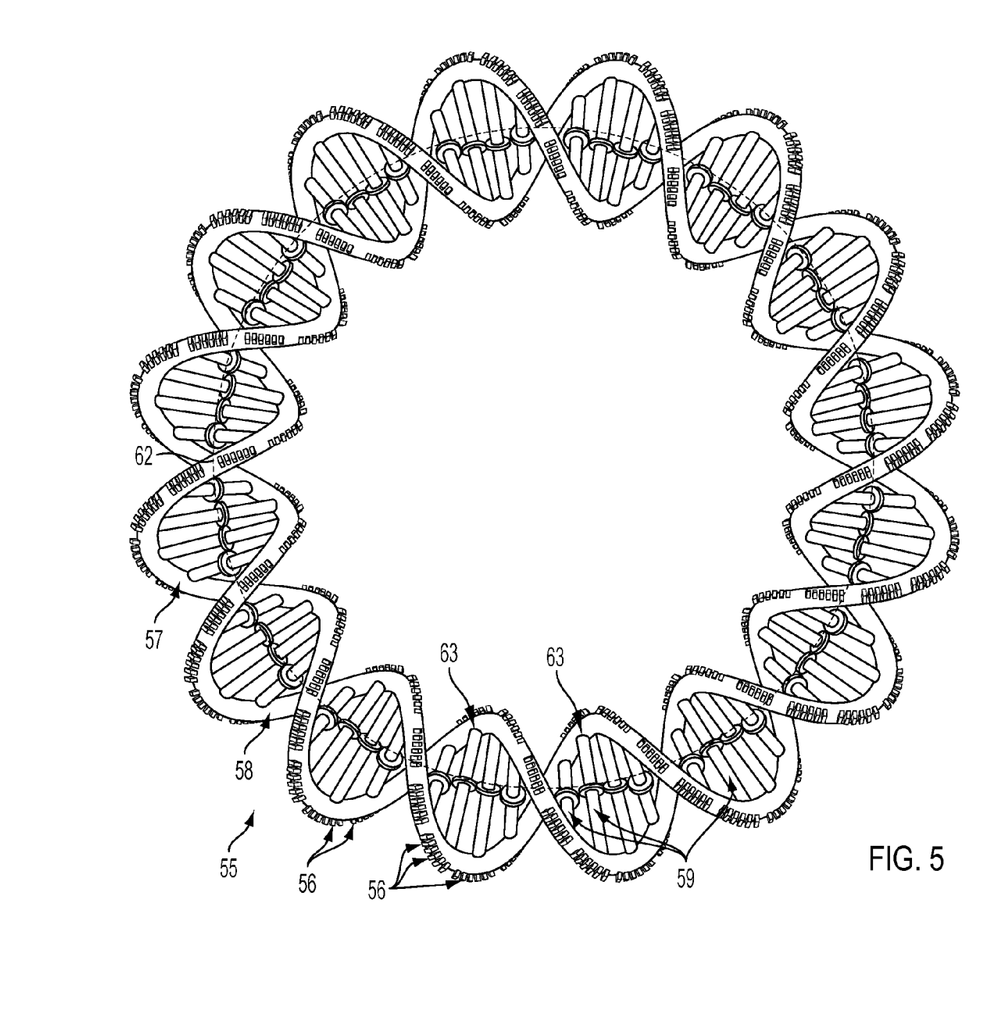
FIG. 5 illustrates a top-down view of an exemplary body including two intertwined helically wound runners sharing the same circular axis and having wire guides, both runners coupled by struts.

FIG. 5 illustrates a top-down view of an exemplary body 55 including two intertwined helically wound runners—runner 57 and runner 58—sharing the same circular axis 62 and having wire guides 56, both runners coupled by struts 59. Though the shape of the cross-section of runner 57 and runner 58 in FIG. 5 may be circular, a runner may still have an inner surface (the half of the surface of a runner for which normal vectors are directed approximately inward toward body 55) and an outer surface (the half of the surface of a runner for which normal vectors are directed approximately outward, away from body 55). Any part of runner 57 or runner 58 may include wire guides 56. Wire guides 56 may include grooves, notches, protrusions, slots, and/or other structural elements disposed on and/or in runner 57 or runner 58 and configured to guide a wire along at least a part of the surface of runner 57 or runner 58, generally in a direction substantially perpendicular to the direction of runner 57 or runner 58 at the point of engagement between one of wire guides 56 and runner 57 or runner 58.

In FIG. 5, one of wire guides 56 of runner 58 may include a protrusion disposed on the outer surface of runner 58, arranged such that wire guide 56 may guide a wire arranged in a helical shape around runner 58, wherein the helical shape has an axis that coincides with runner 58. Such a wire, as any wire listed in any figure included in this description, may be insulated, uninsulated, or partially insulated and partially uninsulated. As shown in FIG. 5, wire guides 56 may be disposed in an intermittent pattern rather than a continuous pattern, e.g. such that no protrusion is disposed on the surface of runner 57 or runner 58 approximately nearest to (or directly opposite to) one of points of engagement 63 between runner 57 or runner 58 and of one struts 59. The number of wire guides per complete revolution of a runner and/or the number of wire guides between adjacent struts may be characteristic measurements/features of body 55. The size, shape, position, and/or pattern of disposition of wire guides 56 may be characteristic measurements/features of body 55.

Figure 6:
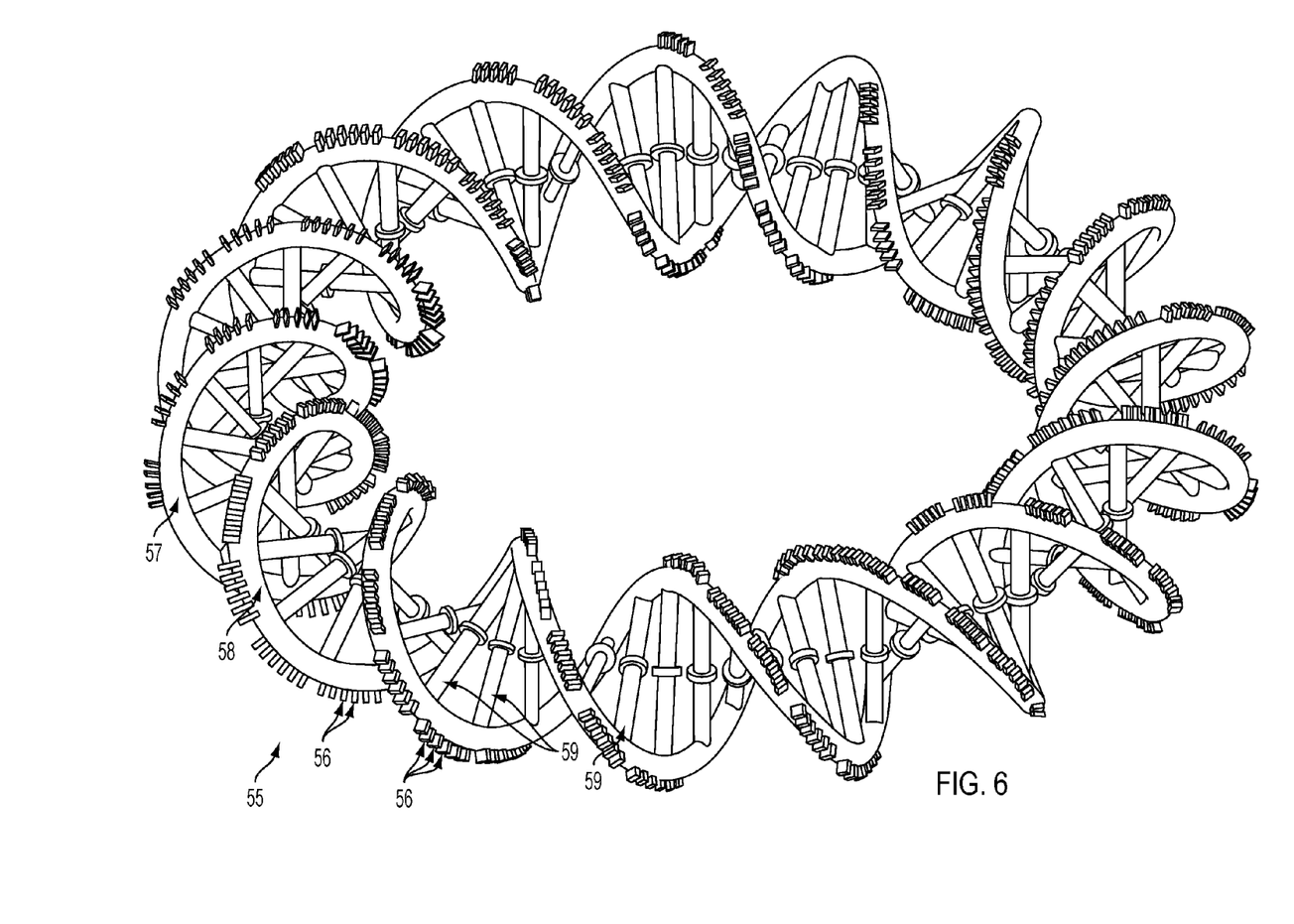
FIG. 6 illustrates an isometric view of an exemplary body including two intertwined helically wound runners sharing the same circular axis and having wire guides, both runner coupled by struts.

FIG. 6 illustrates an isometric view of an exemplary body 55 including two intertwined helically wound runners—runner 57 and runner 58—sharing the same circular axis and having wire guides 56, both runners coupled by struts 59.

Figure 7:
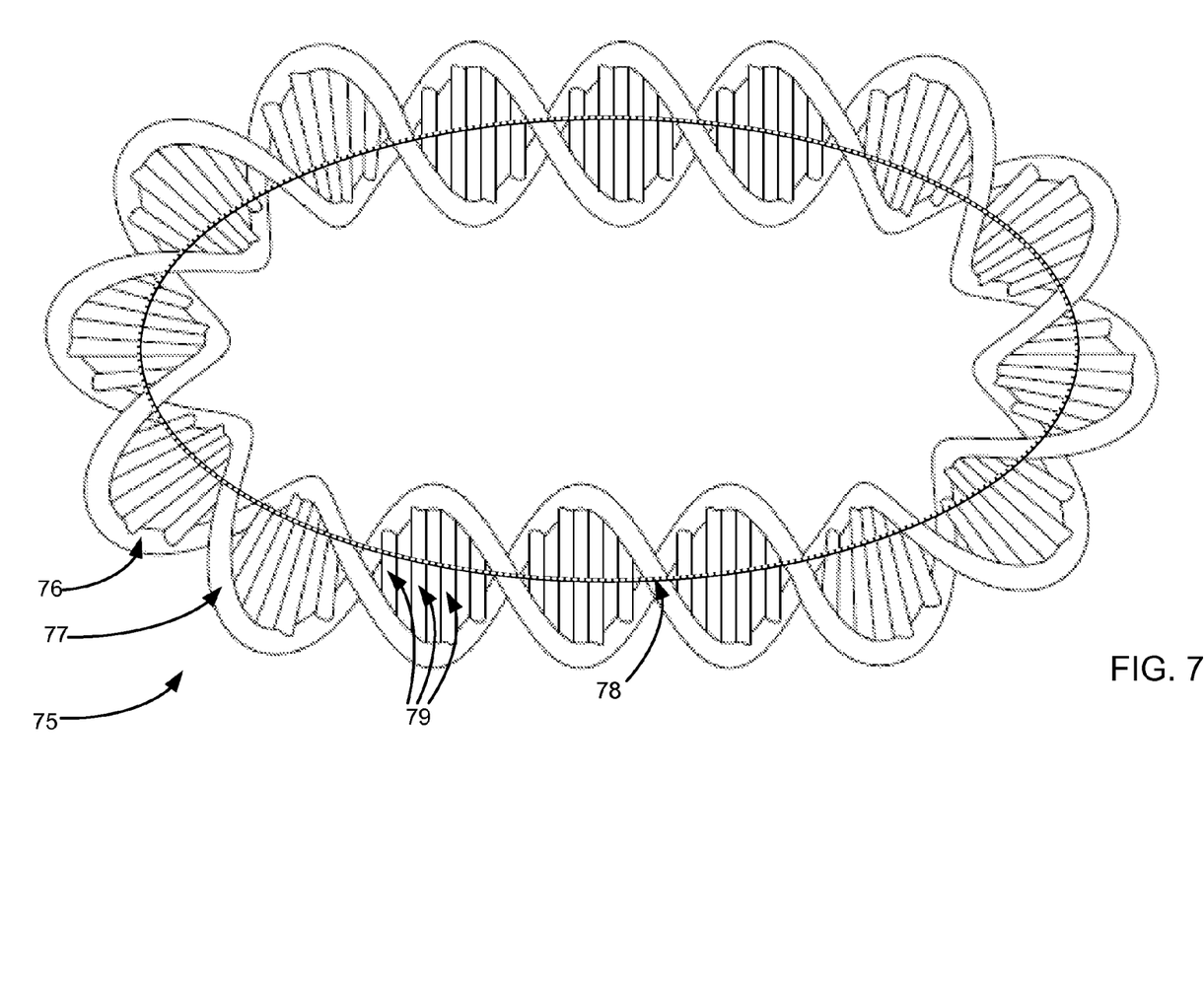
FIG. 7 illustrates a top-down view of an exemplary body including two intertwined helically wound runners sharing the same elliptical axis, both runner coupled by struts.

FIG. 7 illustrates a top-down view of an exemplary body 75 including two intertwined helically wound runners—runner 76 and runner 77—sharing the same elliptical axis 78, both runner coupled by struts 79. A body including two (or more)

intertwined helically wound runners sharing the same axis may be arranged in any planar shape, including a circle, an oval, a triangle, a square, a rectangle, an angular shape, a polygon, and/or other planar shapes. Alternatively, and/or simultaneously, such a body may be arranged in a three-dimensional curve (a.k.a. space curve). In FIG. 7, body 75 may be formed from a body similar to body 15, though comprising more evolutions, by arranging the body in an planar elliptical shape and joining both ends—end 20 and end 21 in FIG. 1—together. The preceding statement is not intended to limit the (process of) manufacture of bodies similar to or substantially the same as body 75 in any way.

Figure 8:
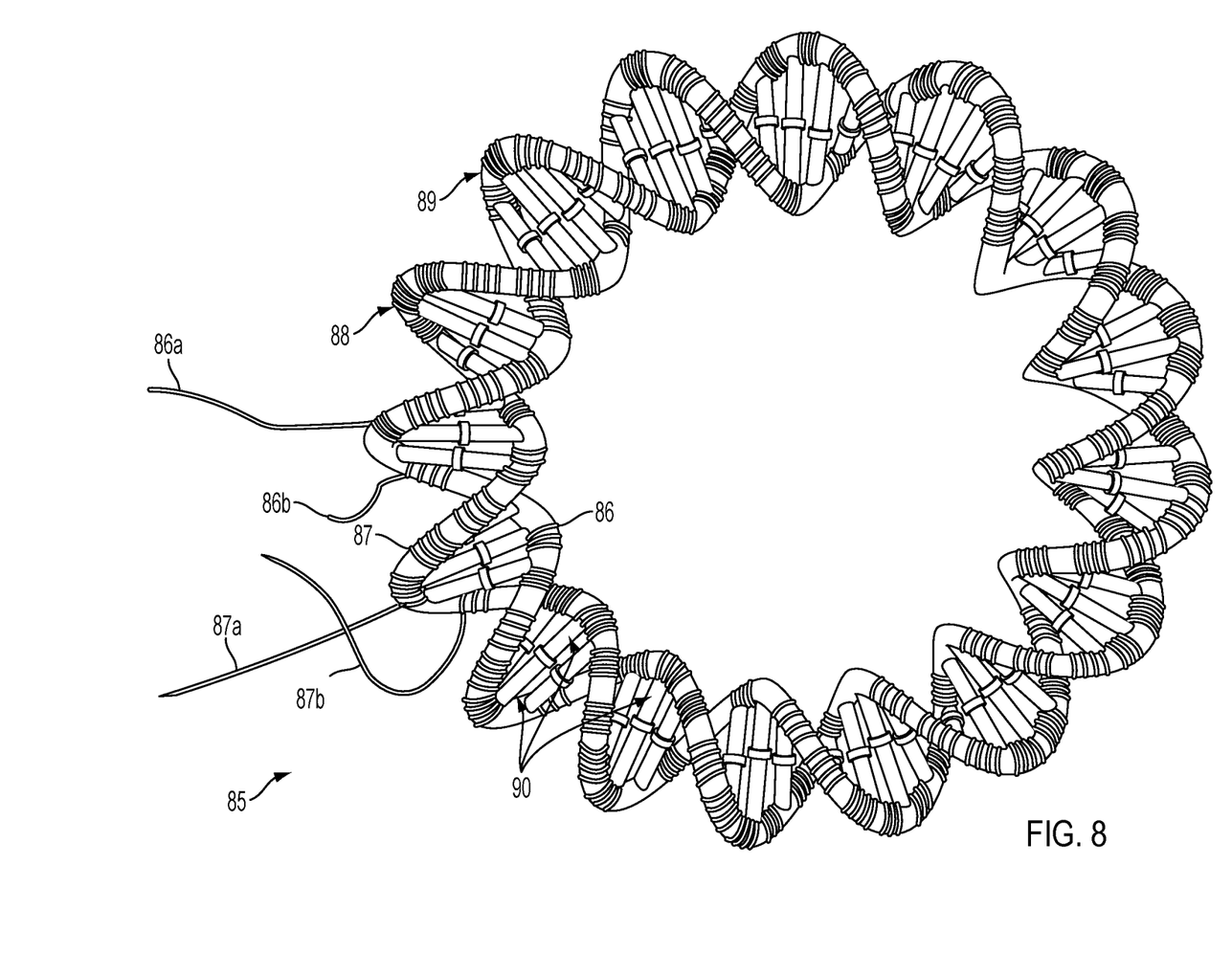
FIG. 8 illustrates a top-down view of an exemplary body including two intertwined helically wound runners sharing the same circular axis, both runners coupled by struts and having conductive wires spirally wound therearound.

FIG. 8 illustrates a top-down view of an exemplary body 85 including two intertwined helically wound runners—runner 88 and runner 89—sharing the same circular axis, coupled by struts 90 and having conductive wires—wire 86 and wire 87—spirally wound therearound. Wire 86 and wire 87, as any wire listed in any figure included in this description, may be insulated, uninsulated, or partially insulated and partially uninsulated. The shape of body 85 may be similar to the shape of body 35 in FIG. 3. Runner 88 and runner 89 of body 85 may form cores around which wire 86 and wire 87 are spirally wound, respectively. As such, wire 86 and wire 87 may be arranged in a helical shape having axes that coincide with runner 88 and runner 89, respectively. As shown in FIG. 8, wire 86 and 87 may be wound such that they go around any of struts 90 of body 85 and/or around any points of engagement between one of struts 90 and one of runners 88 and 89. The number of wire turns per complete revolution of a runner and/or the number of wire turns between adjacent struts may be characteristic measurements/features of body 85. In FIG. 8, wire 86 and wire 87 may be arranged to make approximately five turns between adjacent struts associated with runner 88 and runner 89, respectively, and/or some other number of turns.

Wire 86 may include two leads—lead 86a and lead 86b. Wire 87 may include two leads—lead 87a and lead 87b. Wire 86 and wire 87 may be conductive. Body 85 may be used in an electrical system having one or more power sources and/or current sources arranged such that electrical coupling with one or both of wire 86 and wire 87 may be established, e.g. through coupling with lead 86a and 86b of wire 86 and through coupling with lead 87a and 87b of wire 87. The current supplied to wire 86 may be a direct current or an alternating current. The current supplied to wire 87 may be a direct current or an alternating current. The currents supplied to wire 86 and wire 87 may flow in the same direction or the opposite direction. For alternating currents, operating frequencies ranging from 0 Hz to 40 GHz are contemplated. The operating frequencies for wire 86 and wire 87 may be the same or different. Other electrical operating characteristics of current supplied to wire 86 and wire 87, such as phase, may be the same or different. The electrical system may be used to exploit the electromagnetic field that is created when electrical power is supplied to one or more wires of body 85.

Some embodiments of an electrical system including a body similar to or substantially the same as body 85 in FIG. 8, thus including wire 86 and wire 87, may be configured to have a current in wire 86 flowing in the opposite direction as the current in wire 87. In some embodiments the current supplied to one wire may be a direct current, whereas the current supplied to another wire may be an alternating current.

Figure 9:
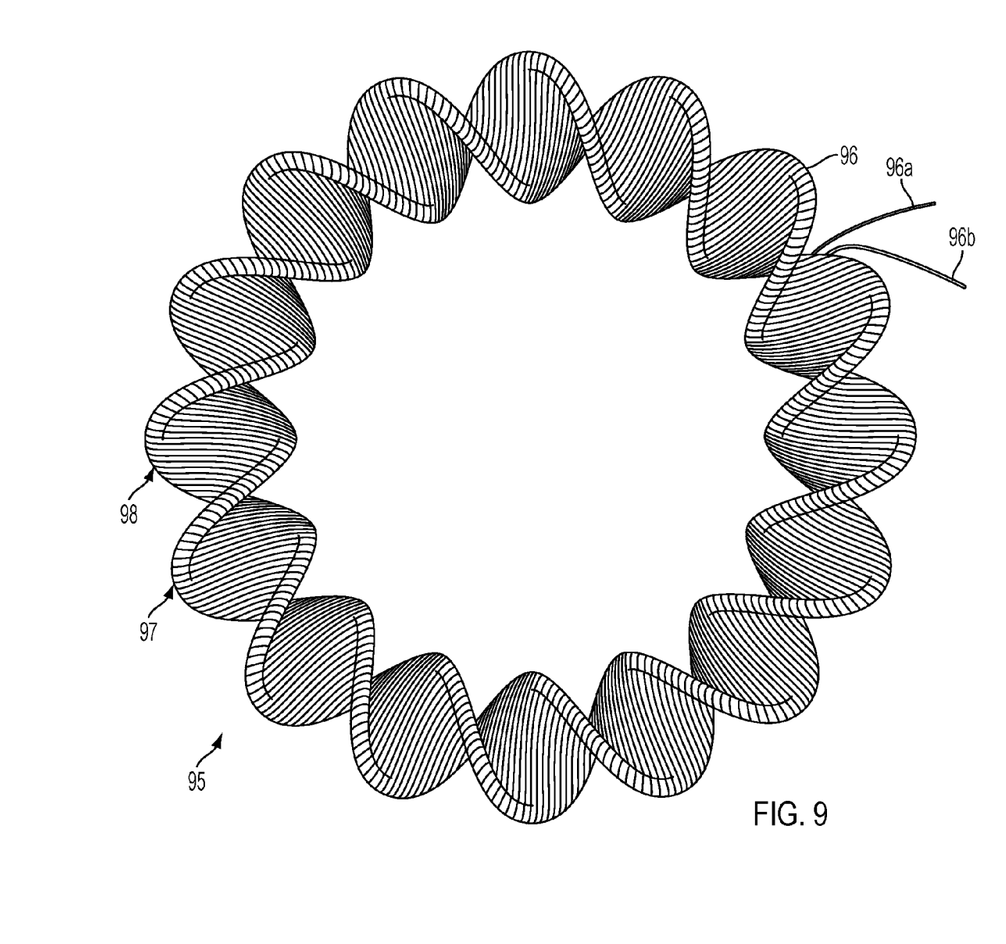
FIG. 9 illustrates a top-down view of an exemplary body including two intertwined helically wound runners sharing the same circular axis, both runner coupled by struts and having a wire spirally wound around both runners of the body.

FIG. 9 illustrates a top-down view of an exemplary body 95 including two intertwined helically wound runners—runner 97 and runner 98—sharing the same circular axis, both runner coupled by struts and having a wire 96 spirally wound around both runners of body 95. Wire 96, as any wire listed in any figure included in this description, may be insulated, uninsulated, or partially insulated and partially uninsulated. Wire 96 may include two leads—lead 86a and lead 86b. The resulting shape of body 95 with wire 96 may be referred to as a helicoidal shape. Wire 96 may be conductive. Body 95 may be used in an electrical system having a power source and/or a current source arranged such that electrical coupling with wire 96, e.g. through leads 96a and 96b, may be established. The electrical power supplied to wire 96 may include a direct current or an alternating current. Operating frequencies for an alternating current flowing through wire 96 are contemplated to range from 0 Hz to 40 GHz. The electrical system may be used to exploit the electromagnetic field that is created when electrical power is supplied to wire 96 of body 95.

Any of the bodies shown in FIGS. 1-9 may be used in an electrical system. Conductive wires may be spirally wound around one or more runners, one or more struts, and/or any combination thereof to produce electrical systems having specific electromagnetic properties when electrical power is supplied to one or more of the conductive wires. These conductive wires may be insulated, uninsulated, or partially insulated and partially uninsulated. A (magnetic) core may be disposed in the space between multiple runners, such that the runners helically wound around the (magnetic)—core. Alternatively, and/or simultaneously, relative to any body described herein, a (magnetic) core may be moved along a straight line, along any curve of the body, along a strut, along a runner, along any axis of the body, or along any surface of the body, in any three-dimensional relation to the body. For example, a magnet may be moved along a line perpendicular to the planar shape of body 85, in the center of the circular axis of body 85, a.k.a. through the "donut-hole."

Applications for any of the electrical systems described herein may include affecting growth and/or growth rate of plants and/or other organisms. Applications for any of the electrical systems described herein may include therapeutic applications. Applications for any of the electrical systems described herein may include energy production, conversion, and/or transformation. Applications for any of the electrical systems described herein may include ATP production, transfer, and/or processing.

In some embodiments, an electrical system including any of the bodies shown in FIGS. 1-9 may be used as a component in an electrical circuit, performing one or more functions and/or applications including a (tunable) inductor, a (Tesla) coil, a transformer, a transducer, a transistor, a resistor, a solenoid, a stator for an electrical motor, an electromagnet, an electromagnetic pulse generator, an electromagnetic actuator, an energy conversion device, a position servomechanism, a generator, a stepping motor, a DC motor, a (contact-free) linear drive, an axial flux device, a measurement device for magnetic permeability, a dipole magnet, and a device to alter electron and/or particle trajectory.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An electrical system comprising:
a body including a runner, wherein the runner is arranged in a first helical shape, wherein the body is arranged in a toroidal shape; and
a conductive wire wound around the runner of the body in multiple revolutions such that the conductive wire is arranged in a second helical shape formed around the first helical shape of the runner, wherein the conductive wire is arranged at a fixed distance from the runner for individual ones of the multiple revolutions.

2. The electrical system of claim 1, wherein the first helical shape of the runner is arranged within the second helical shape of the conductive wire.

3. The electrical system of claim 1, wherein the first helical shape and the second helical shape have the same handedness.

4. The electrical system of claim 1, wherein the first helical shape and the second helical shape both have right-handedness.

5. The electrical system of claim 1, wherein the first helical shape has a first axis, wherein the second helical shape has a second axis, and wherein the second axis coincides with the runner.

6. The electrical system of claim 1, wherein the runner is arranged in between 2 and 10000 revolutions in the body.

7. The electrical system of claim 1, wherein the conductive wire is arranged in between 2 and 10000 revolutions per revolution of the first helical shape of the runner.

8. The electrical system of claim 1, further comprising:
an alternating current source arranged to electrically couple with the conductive wire such that an electromagnetic field is generated, wherein the alternating current source operates above 0 Hz and below 40 GHz.

9. The electrical system of claim 1, wherein the body includes a second runner, wherein the second runner is arranged in a third helical shape that is intertwined with the first helical shape, the electrical system further comprising:
a second conductive wire wound around the second runner of the body such that the second conductive wire is arranged in a fourth helical shape formed around the third helical shape of the second runner.

10. The electrical system of claim 9, wherein the third helical shape of the second runner is arranged within the fourth helical shape of the second conductive wire.

11. The electrical system of claim 9, wherein the first helical shape, the second helical shape, the third helical shape, and the fourth helical shape have the same handedness.

12. An electrical system comprising:
a body including two intertwined helically wound runners, wherein the runners include a first runner and a second runner, wherein the first runner has a first helical shape, wherein the second runner has a second helical shape, wherein the body is arranged in a toroidal shape, and wherein the first runner and the second runner are arranged in a shape of a double helix;
a first conductive wire wound around the first runner of the body such that the first conductive wire is arranged in a third helical shape formed around the first helical shape of the first runner, wherein the first helical shape is arranged within the third helical shape;
a second conductive wire wound around the second runner of the body such that the second conductive wire is arranged in a fourth helical shape formed around the second helical shape of the second runner, wherein the second helical shape is arranged within the fourth helical shape; and
a current source arranged to electrically couple with the first conductive wire and the second conductive wire, wherein the current source is configured to supply electrical power to the first conductive wire and the second conductive wire such that an electromagnetic field is generated.

13. An electrical system comprising:
a body including a runner and a second runner, wherein the runner is arranged in a first helical shape, wherein the body is arranged in a toroidal shape; and
a conductive wire wound around the runner of the body such that the conductive wire is arranged in a second helical shape formed around the first helical shape of the runner,
wherein the second runner is arranged in a third helical shape that is intertwined with the first helical shape, wherein the runner and the second runner are arranged in a shape of a double helix, the electrical system further comprising:
a second conductive wire wound around the second runner of the body such that the second conductive wire is arranged in a fourth helical shape formed around the third helical shape of the second runner.

14. The electrical system of claim 13, wherein the third helical shape of the second runner is arranged within the fourth helical shape of the second conductive wire.

15. The electrical system of claim 13, wherein the first helical shape, the second helical shape, the third helical shape, and the fourth helical shape have the same handedness.

16. An electrical system comprising:
a body including a runner, wherein the runner is arranged in a first helical shape, wherein the body is arranged in a toroidal shape; and
a conductive wire wound around the runner of the body in multiple revolutions such that the conductive wire is arranged in a second helical shape formed around the first helical shape of the runner, wherein the conductive wire is arranged in continuous contact with the runner for individual ones of the multiple revolutions.

* * * * *